(12) United States Patent
Focht et al.

(10) Patent No.: US 7,981,086 B2
(45) Date of Patent: Jul. 19, 2011

(54) SURGICAL ACCESS ASSEMBLY WITH WINEPRESS SEAL

(75) Inventors: Kenneth Allen Focht, Needham, MA (US); Jared Alden Judson, Topsfield, MA (US); Oivind Brockmeier, Sommerville, MA (US)

(73) Assignee: Tyco Healthcare Group LP, New Haven, CT (US)

( * ) Notice: Subject to any disclaimer, the term of this patent is extended or adjusted under 35 U.S.C. 154(b) by 237 days.

(21) Appl. No.: 12/124,584

(22) Filed: May 21, 2008

(65) Prior Publication Data
US 2008/0294125 A1 Nov. 27, 2008

Related U.S. Application Data

(60) Provisional application No. 60/931,935, filed on May 24, 2007.

(51) Int. Cl.
*A61M 5/178* (2006.01)
(52) U.S. Cl. .............. 604/167.01; 604/164.01; 604/256; 604/167.06; 604/167.03
(58) Field of Classification Search ............. 604/164.01, 604/251–256, 264, 167.01–167.06
See application file for complete search history.

(56) References Cited

U.S. PATENT DOCUMENTS

| | | |
|---|---|---|
| 4,978,341 A | 12/1990 | Niederhauser |
| 5,030,206 A | 7/1991 | Lander |
| 5,053,016 A | 10/1991 | Lander |
| 5,059,186 A | 10/1991 | Yammamoto et al. |
| 5,108,380 A | 4/1992 | Herlitze et al. |
| 5,197,955 A | 3/1993 | Stephens |
| 5,263,944 A | 11/1993 | Vidal et al. |
| 5,304,143 A | 4/1994 | Green et al. |
| 5,308,336 A | 5/1994 | Hart et al. |
| 5,334,164 A | 8/1994 | Guy |
| 5,342,315 A | 8/1994 | Rowe |
| 5,350,364 A * | 9/1994 | Stephens et al. ......... 604/167.06 |
| 5,366,445 A | 11/1994 | Haber |
| 5,385,552 A | 1/1995 | Haber |
| 5,385,553 A | 1/1995 | Hart |

(Continued)

OTHER PUBLICATIONS

European Search Report dated Sep. 1, 2008, Application No. EP 08 25 1792.

(Continued)

*Primary Examiner* — Theodore J Stigell
*Assistant Examiner* — Edelmira Bosques

(57) ABSTRACT

A surgical access apparatus includes a housing, an access member extending from the housing and having a longitudinal passageway for passage of an object and defining trailing and leading ends and an elongated seal mechanism mounted relative to the housing. The elongated seal mechanism includes a trailing hub and a leading hub longitudinally spaced from the trailing hub, and being adapted for relative rotational movement about the longitudinal axis, a plurality of spokes extending between and connected to the trailing hub and the leading hub, and an elongated seal member disposed within the spokes and adapted to establish a sealing relation about the object. The spokes define a first minimum internal dimension in a first condition thereof in the absence of an object and defining a second minimum internal dimension in a second condition thereof upon insertion of the object and relative rotation of the trailing hub and the leading hub. The second minimum internal dimension is greater than the first minimum internal dimension. The at least two of the spokes are generally obliquely arranged at a first angle relative to the longitudinal axis when in the first condition thereof and are adapted to be generally arranged at a second angle relative to the longitudinal axis when in the second condition thereof, the second angle being less than the first angle.

13 Claims, 5 Drawing Sheets

U.S. PATENT DOCUMENTS

| | | |
|---|---|---|
| 5,389,081 A | 2/1995 | Castro |
| 5,391,153 A | 2/1995 | Haber |
| 5,391,154 A | 2/1995 | Young |
| 5,397,314 A | 3/1995 | Farley |
| 5,407,433 A | 4/1995 | Loomas |
| 5,411,483 A | 5/1995 | Loomas |
| 5,417,705 A | 5/1995 | Haber |
| 5,429,609 A | 7/1995 | Yoon |
| 5,441,486 A | 8/1995 | Yoon |
| 5,496,280 A | 3/1996 | Vandenbroek |
| 5,538,509 A | 7/1996 | Dunlap |
| 5,545,142 A | 8/1996 | Stephens |
| 5,549,565 A | 8/1996 | Ryan |
| 5,603,702 A | 2/1997 | Smith |
| 5,634,908 A | 6/1997 | Loomas |
| 5,657,963 A | 8/1997 | Hinchliffe |
| 5,685,854 A | 11/1997 | Green |
| 5,709,664 A | 1/1998 | Vandenbroek |
| 5,720,759 A | 2/1998 | Green |
| 5,792,113 A | 8/1998 | Kramer |
| 5,814,026 A | 9/1998 | Yoon |
| 5,827,228 A | 10/1998 | Rowe |
| 5,895,377 A | 4/1999 | Smith |
| 5,913,847 A * | 6/1999 | Yoon .......................... 604/523 |
| 5,989,233 A | 11/1999 | Yoon |
| RE36,702 E | 5/2000 | Green |
| 6,083,203 A | 7/2000 | Yoon |
| 6,099,505 A | 8/2000 | Ryan |
| 6,171,299 B1 | 1/2001 | Bonutti |
| 6,358,266 B1 | 3/2002 | Bonutti |
| 6,482,181 B1 | 11/2002 | Racenet |
| 6,551,282 B1 | 4/2003 | Exline |
| 6,595,946 B1 | 7/2003 | Pasqualucci |
| 6,702,787 B2 | 3/2004 | Racenet et al. |
| 6,811,546 B1 | 11/2004 | Callas |
| 6,923,783 B2 | 8/2005 | Pasqualucci |
| 6,942,671 B1 | 9/2005 | Smith |
| 7,011,314 B2 | 3/2006 | McFarlane |
| 7,025,747 B2 | 4/2006 | Smith |
| 7,083,626 B2 | 8/2006 | Hart |
| 7,169,130 B2 | 1/2007 | Exline |
| 7,244,244 B2 | 7/2007 | Racenet |
| 7,276,075 B1 | 10/2007 | Callas |
| 7,390,317 B2 | 6/2008 | Taylor |
| 7,438,702 B2 | 10/2008 | Hart |
| 7,470,255 B2 | 12/2008 | Stearns |
| 2005/0092944 A1* | 5/2005 | Patterson .......................... 251/4 |
| 2006/0071432 A1 | 4/2006 | Staudner |

OTHER PUBLICATIONS

European Search Report for corresponding EP 08251792 date of mailing is Sep. 8, 2008 (3 pages).
US 7,282,043, 10/2007, Racenet (withdrawn)

* cited by examiner

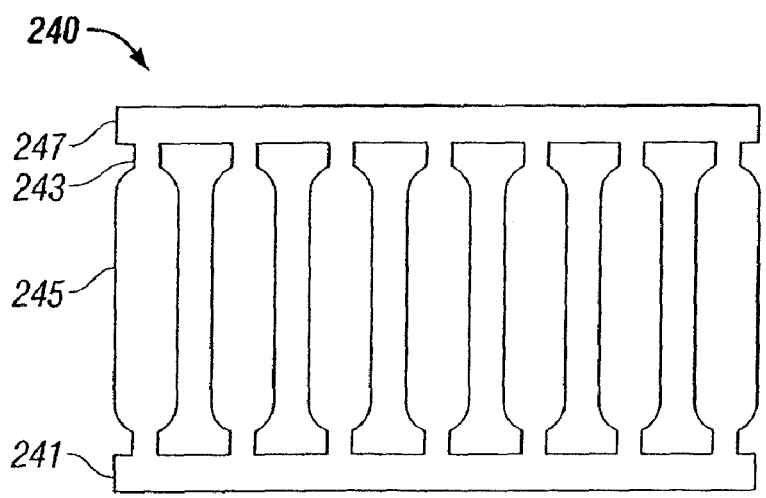
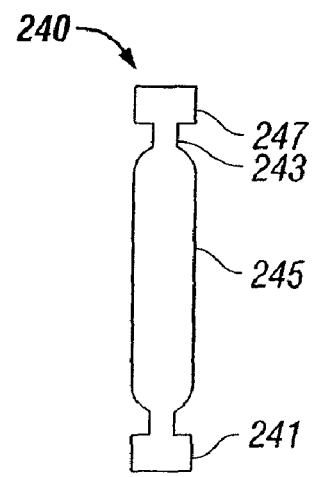
*FIG. 5A*  *FIG. 5B*
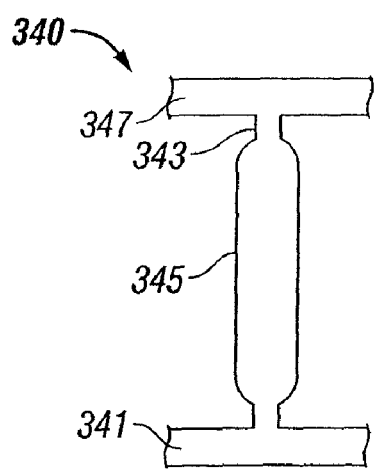
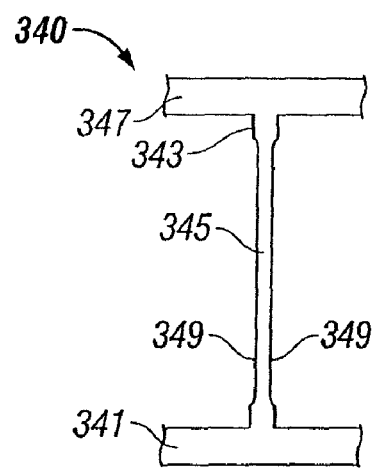
*FIG. 6A*  *FIG. 6B*

SURGICAL ACCESS ASSEMBLY WITH WINEPRESS SEAL

CROSS REFERENCE TO RELATED APPLICATION

The present application claims the benefit of and priority to U.S. Provisional Application Ser. No. 60/931,935 filed on May 24, 2007, the entire contents of which are incorporated herein by reference.

BACKGROUND

1. Technical Field

The present disclosure relates to a surgical access apparatus for permitting the introduction of a surgical instrument into a body cavity. In particular, the disclosure relates to a seal assembly for the access apparatus and being adapted to form a seal about a surgical instrument while centering the surgical instrument within the apparatus.

2. Background of Related Art

There are many different types of minimally invasive surgical procedures whereby a surgeon gains access to an internal surgical site through a small opening in the body. For example, a laparoscopic procedure involves the insertion of instruments through a small opening in a patient's abdomen. Also, an arthroscopic procedure allows a surgeon to examine the interior of a patient's joint through a small incision in the skin. A comprehensive term, used throughout the present disclosure to refer to this type of procedure, is endoscopic surgery.

Typically in an endoscopic surgery, a small incision is made in the skin and a cannula is inserted through the fascia into a body opening. A cannula is a narrow tube, typically 5 to 13 mm in diameter, which serves generally to hold the incision open and provide a conduit to the body cavity through which a surgeon may introduce and withdraw the various surgical instruments required by the desired procedures. An insufflation gas (most commonly carbon dioxide) may be introduced through the cannula into the body opening establishing a slight pressure. This practice inflates the body opening and provides a viewing space wherein a surgeon may insert a camera lens to monitor the procedure. The surgeon may then use the insufflated space to maneuver a variety of other instruments into position to manipulate the targeted tissue without contacting and damaging the surrounding tissue.

Of primary concern in these procedures is establishing a fluid tight seal across the cannula to maintain the integrity of the insufflated body cavity. To maintain the insufflation pressure and the corresponding working space, many types of seals have been introduced. One common difficulty with conventional seals is the inability of the seal to accommodate the entire range of instruments necessary to complete a surgical procedure. A single surgical procedure will often require many instruments having dissimilar diameters. To ensure that a fluid-tight connection with each of these instruments is achieved, a surgeon might need to select an instrument seal having an aperture sized slightly smaller than the smallest diameter instrument to be used. Because the instrument seal is elastomeric, it is possible the aperture will be able to expand sufficiently to accept the largest diameter instrument, but there will be some associated difficulty. There is a friction force associated with moving the instrument while it is in contact with the aperture of the instrument seal. This friction force is sometimes called an insertion or glide force, and it must be kept low enough such that manipulating the instrument is not awkward for the surgeon. Inserting a large diameter instrument into a small diameter aperture will likely cause insertion and glide forces which are too large to be appropriate for the endoscopic procedures which often involve delicate movements.

One simple solution to this problem is to provide an instrument seal which is removable during surgery. In this way, a surgeon could select the instrument seal sized most appropriately for each instrument and install the seal just before use. Although effective, this process can be time consuming and unnecessarily prolong the surgery. Some devices have been introduced to hasten this process such as a smaller diameter instrument seal that can be flipped into and out of position with a simple movement positioned proximally in relation to a conventional stationary large diameter instrument seal. This type of system is most effective for use with a limited number of instruments having diameters very close to one of the two instrument seal apertures, but, a surgeon may still encounter difficulty with insertion forces or maintaining a seal with intermediately sized instruments.

Besides the accommodation of instruments of varying diameter, another characteristic desirable in an instrument seal is the ability of the seal to provide radial support to an instrument. Adequate radial support will aid in stabilizing the instrument so a surgeon will not need to divert attention from the surgical procedure to hold the instrument steady. Radial support is often provided by the very same features in a seal which assist in centering the instrument since providing a robust radial support at all points around the diameter of an instrument will naturally tend to keep the instrument centered. A need exists for an instrument seal capable of centering an elongated object and having an aperture that is truly flexible and modifiable in use. The seal should be able to accommodate an entire range of variously sized instruments without requiring any awkward manipulations to be performed by a surgeon.

SUMMARY

Accordingly, the present disclosure is directed to a surgical access apparatus. The surgical apparatus includes a housing, an access member extending from the housing and having a longitudinal passageway for passage of an object and defining trailing and leading ends and an elongated seal mechanism mounted relative to the housing. The elongated seal mechanism includes a trailing hub and a leading hub longitudinally spaced from the trailing hub, and being adapted for relative rotational movement about the longitudinal axis, a plurality of spokes extending between and connected to the trailing hub and the leading hub, and an elongated seal member disposed within the spokes and adapted to establish a sealing relation about the object. The spokes define a first minimum internal dimension in a first condition thereof in the absence of an object and defining a second minimum internal dimension in a second condition thereof upon insertion of the object and relative rotation of the trailing hub and the leading hub. The second minimum internal dimension is greater than the first minimum internal dimension. The at least two of the spokes are generally obliquely arranged at a first angle relative to the longitudinal axis when in the first condition thereof and are adapted to be generally arranged at a second angle relative to the longitudinal axis when in the second condition thereof, the second angle being less than the first angle.

The trailing hub and the leading hub are adapted for relative longitudinal movement when transitioning of the spokes between the first and second conditions. The spokes are normally biased toward the first condition thereof. The seal member may be arranged to normally bias the spokes toward the first condition thereof. The seal member includes trailing and leading flanges. The trailing and leading flanges are adapted to engage the trailing and leading hubs, respectively, to normally bias the trailing and leading hubs in a longitudinal direction toward each other corresponding to the first condition of the spokes.

The elongated seal mechanism includes an outer liner circumferentially disposed about the spokes and fixed from rotational movement relative to the longitudinal axis. The outer liner is engageable with one hub of the trailing and leading hubs during insertion and withdrawal of the object to prevent rotational movement of the one hub whereby the other hub is free to rotate to permit transitioning of the spokes between the first and second condition thereof. The outer liner is dimensioned to be engaged by the trailing hub during insertion of the object and cooperates to fix the trailing hub from rotation whereby the leading hub rotates and longitudinally moves relative to the trailing hub to permit the spokes to assume the second condition. The outer liner may be dimensioned to be engaged by the leading hub during withdrawal of the object and cooperates to fix the leading hub from rotation whereby the trailing hub rotates and longitudinally moves relative to the leading hub to facilitate withdrawal of the object. The outer liner may be dimensioned to engage and fix each of the trailing and leading hubs from rotational movement when in the first condition thereof.

The leading hub is adapted to longitudinally move in a leading direction during insertion of the object to disengage the outer liner to thereby rotate relative to the trailing hub and permit the spokes to transition from the first condition to the second condition. The trailing hub is adapted to longitudinally move in a trailing direction during withdrawal of the object to disengage the outer liner to thereby rotate relative to the leading hub and facilitate removal of the object.

Each of the spokes may be connected to the leading and trailing hubs by a living hinge. The spokes may be adapted to normally bias the object in general alignment with the longitudinal axis.

The apparatus incorporates the structure of an ancient toggle-action winepress to accomplish the movements described above and accommodate instruments of varying diameter without the need to replace seal parts. In its simplest form a toggle-action linkage includes two rigid members hinged at an angle in the center and supported on the ends with sliders allowing motion with one degree of freedom. Appropriately applying a force to the hinge will have a tendency to straighten out the linkage to provide a mechanical advantage at the two ends which will travel a shorter distance than the hinge, but with greater force. Combining this straightening-out principal with a mechanism for rotary motion will yield a device much like the ancient winepress described in HARRY WALTON, THE HOW AND WHY OF MECHANICAL MOVEMENTS; EXACTLY HOW MACHINES WORK: ENGINES, TURBINES, TRANSMISSIONS, BRAKES, CLUTCHES, ROCKETS, ATOMIC GENERATORS, GYROSCOPES, GUIDANCE SYSTEMS, pp. 25-27, E.P. Dutton & Co., NY 1968. The structure includes a large capstan capable of rotating relative to the top brace to which it is attached on the underside. The top brace is rigidly connected to a base plate by a pair of round vertical bars which also provide a bearing surface for a sliding platen disposed between the base plate and the top brace. The top surface of the sliding platen is equipped with a circular array of sockets corresponding with a similar array on the lower face of the capstan. Two spokes are disposed obliquely between the capstan and the sliding platen, each with an upper end within a socket on the capstan and a lower end in a socket on the sliding platen. The capstan is equipped with a long handle which allows a pressman to turn the capstan, thereby straightening out the spokes and forcing the sliding platen downward toward the base plate where grapes are awaiting pressing.

The operation of the winepress exhibits a complex motion in the spokes. The upper ends of the spokes rotate with respect to a vertical axis about which the capstan turns while remaining at the same vertical elevation. On the other hand, the lower ends of the spokes translate downward while remaining at the same radial position. This motion straightens out the rigid spokes with respect to the vertical axis providing the mechanical advantage of a toggle-action mechanism. As the spokes are straightened out, the relative spacing of the top ends of the spokes remains constant as does the relative spacing at the lower ends. The relative spacing between the midpoints of the two spokes, however, will increase. It is this dispersal of the midpoints that makes the winepress motion particularly useful in designing an adjustable seal to accommodate larger and larger instruments. Additionally, if the winepress capstan were turned in an opposite direction, the spokes would lean over causing the sliding platen to rise while the relative spacing between the midpoints decreased. This radial congregation of the midpoints is useful for a seal accommodating smaller diameter instruments.

Increasing the number of rigid spokes arranged obliquely in a circular array around a central longitudinal axis can produce a conceptually useful geometry. The surface formed by the spokes as the number of spokes approaches infinity resembles a hyperboloid of one sheet. This surface has an hourglass profile with a narrow throat diameter in the center, which can be modified by the motion of the spokes. Straightening out the spokes elongates the hourglass, opening the throat until the spokes are completely vertical and the surface resembles a cylinder. Leaning the spokes compresses the hourglass, thereby closing the throat. In any configuration, the narrowest throat diameter would always be defined by the midpoints of the spokes.

Generally stated, the present disclosure relates to a winepress seal for a cannula assembly which may exhibit components mimicking the movements of the winepress spokes and components having an adjustable hourglass profile. The winepress seal employs these features to selectively create a fluid-tight connection with variously sized surgical instruments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 5A is a front view of an unrolled spoke tube of the winepress seal assembly;

FIG. 5B is a side plan view of an individual spoke of the spoke tube of FIG. 5A;

FIG. 6A is front plan view of a bladed spoke; and

FIG. 6B is a side plan view of the bladed spoke of FIG. 6A.

DETAILED DESCRIPTION OF PREFERRED EMBODIMENTS

Figure 1:
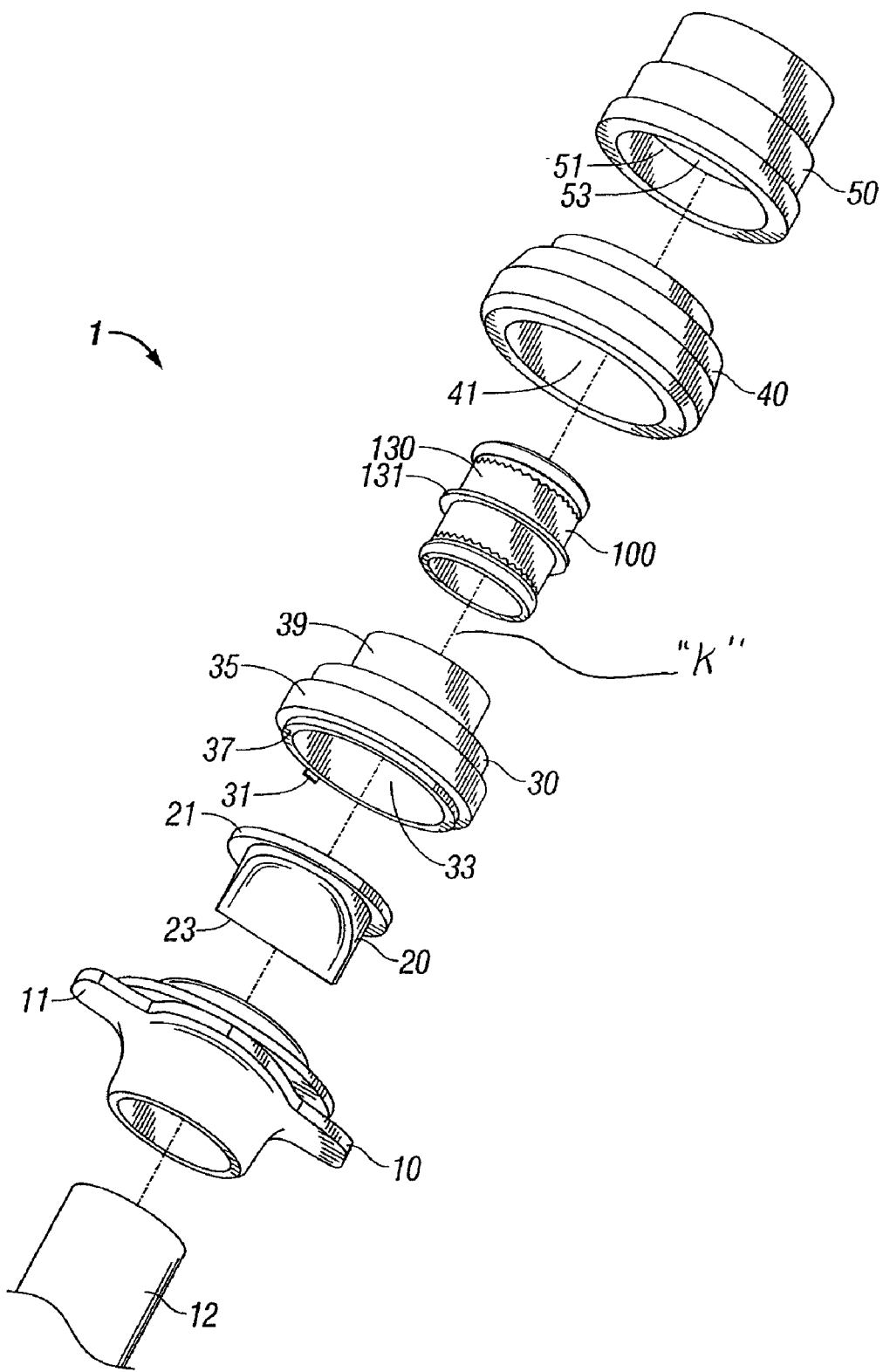
FIG. 1 is an exploded perspective view of a cannula assembly incorporating a dual seal system constructed in accordance with the present disclosure.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on the surgical device or instrument which is closer to the operator, while the term "distal" will refer to the direction away from the operator or a relative position on the instrument which is further from the operator.

Referring initially to FIG. 1, the dual seal system of cannula assembly 1 in accordance with the principals of the present disclosure is illustrated. The dual seal system includes winepress seal assembly 100 which is adapted to form a seal about a surgical object. Cannula assembly 1 includes a bottom housing 10 which is configured to mount or accept a cannula 12 on its distal side. The cannula 12 is intended to be partially inserted into a body cavity through a small incision in the skin to provide access to the body cavity. Bottom housing 10 includes diametrically opposed extensions 11 which provide a surface for an operator to grip the cannula assembly 1 with two fingers. An interior ledge within bottom housing 10 supports flange 21 on duckbill valve 20. Duckbill valve 20 is an elastomeric member with a pair of distally extending substantially flat lips 23 which are normally biased together to create a substantial fluid-tight seal through the cannula in the absence of an instrument. Lips 23 may be easily separated upon the insertion of an instrument from the proximal side.

Winepress support 30 includes central opening 33 extending from its distal end to its proximal end, and tab 31 configured for attachment to bottom housing 10. Ridge 37 is disposed about central opening 33 such that when winepress support 30 is connected to bottom housing 10, ridge 37 abuts the proximal face of flange 21 of duckbill valve 20 creating a substantially fluid-tight interface. Support column 39 is hollow and encircles central opening 33 on the proximal side of the winepress support 30. Central opening 33 is configured to slidingly accept winepress assembly 100 up to a distal face of support ring 131 of liner 130.

Upper housing 40 includes central bore 41 configured to encompass winepress seal assembly 100 when top housing 40 is connected to bottom housing 10 by any conventional means. Central passageway 51 of cap 50 is configured to slidingly engage the winepress assembly 100 down to a proximal face of support ring 131 of liner 130 of the winepress seal assembly 100. An interior rim 53 disposed within central passageway 51 abuts the proximal face of support ring 131 of winepress assembly 130. Although certain parts of winepress assembly 100 are capable of relative motions as described in greater detail below, liner 130 is held securely in position because its support ring 131 is disposed between the support column 39 of winepress support 30 and the interior rim 53 of cap 50. Cap 50 may be securely attached to the top housing 40 by any conventional means and may be configured to make a snap fit connection. Central passageway 51 extends to the proximal side of cap 50 and permits entry of an elongated object into the winepress assembly 100. The cannula assembly 1 contains a central corridor which is only closed by lips 23 on duckbill valve 20.

Figure 2:
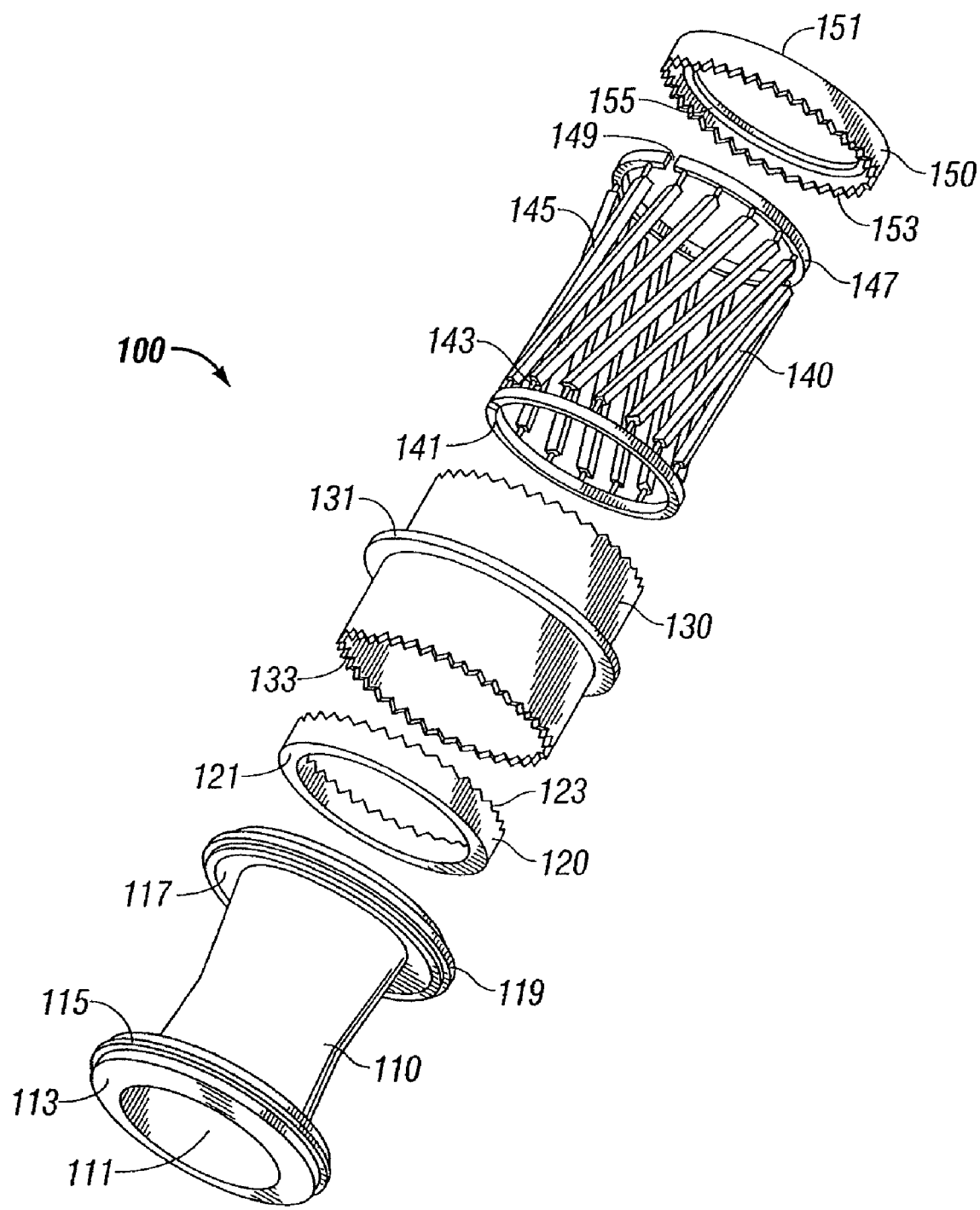
FIG. 2 is an exploded perspective view of the winepress seal assembly of FIG. 1.

Referring now to FIG. 2, in conjunction with FIG. 1, the winepress assembly 100 of the present disclosure will be described in greater detail. Winepress assembly 100 includes an elastomeric seal 110, a lower or leading end cap 120, a liner 130, a spoke tube 140, and an upper or trailing end cap 150. Each component of winepress assembly 100 is in general alignment with the central longitudinal axis "k" of cannula 1 and includes a central shaft which allows an elongated object to pass through.

Elastomeric seal 110 includes throat 111 which extends the entire length of elastomeric seal 110 to accept an elongated object inserted there through. Elastomeric seal 110 is bowed inward near its midpoint to give it an hourglass shape such that a minimum interior throat diameter near the center may sealingly engage the elongated object. As discussed below, the flexibility of elastomeric seal 110 allows the minimum interior throat diameter to be modified to be used with variously sized objects. Also included on elastomeric seal 110 are lower and upper collars 113, 117 protruding radially from the throat 111 at the distal or leading and proximal or trailing ends, respectively. Lower and upper collars 113, 117 include lower and upper beads 115, 119 protruding from their exterior surfaces. The beads define a maximum outer dimension of the elastomeric seal 110 and are each adapted to create a seal around the periphery of their respective collar 113, 117. Lower bead 115 is adapted to sealingly and slidingly engage an interior surface of central opening 33 in winepress support 30 such that longitudinal translation of lower collar 113 will not compromise the seal within the winepress assembly 100. Upper bead 119 is adapted to similarly engage an interior surface of the central passageway 51 through cap 50.

The throat 111 of elastomeric seal 110 is intended to be the innermost component radially of winepress seal 100. Radially surrounding the throat 111 and between the collars 113, 117 is spoke tube 140. Spoke tube 140 includes an array of spokes 145, connected by hinges 143 to leading hub 141 and trailing hub 147. A proximal face on trailing hub 147 abuts a shelf 155 on upper end cap 150, while a distal face of leading hub 141 abuts a similar shelf (not visible) on lower end cap 120. The end caps 120, 150 may be rigidly attached to the hubs 141, 147 by any conventional means including an appropriate adhesive. In one embodiment, end caps 120, 150 are respectively secured to the hubs 141, 147 in a manner which may prevent rotational movement of the secured components. Lower end cap 120 includes a flat face 121 on its distal side and an array of teeth 123 on the opposite side. Similarly, upper end cap 150 includes a flat face 151 on its proximal end and an array of teeth 153 on its distal end. End caps 120, 150 may be identical parts disposed with opposite orientations. Radially surrounding the spoke tube 140 and disposed longitudinally between the end caps 120, 150 is liner 130. Liner 130 includes support ring 131 and an array of notches 133 along the proximal and distal faces. Support ring 131 is sandwiched between cap 50 and support column 39 of winepress support 30 to hold the liner 130 firmly in position.

Figure 3A:
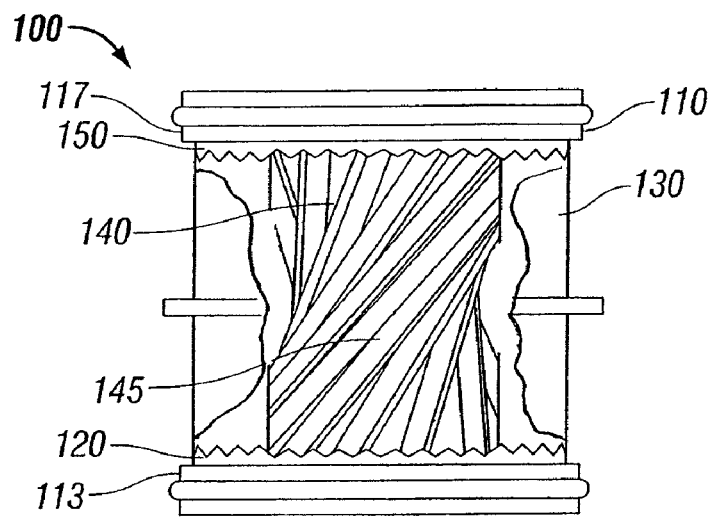
FIG. 3A is an enlarged side view with portions cut-away of the winepress seal assembly in a first condition in the absence of an instrument.
Figure 3B:
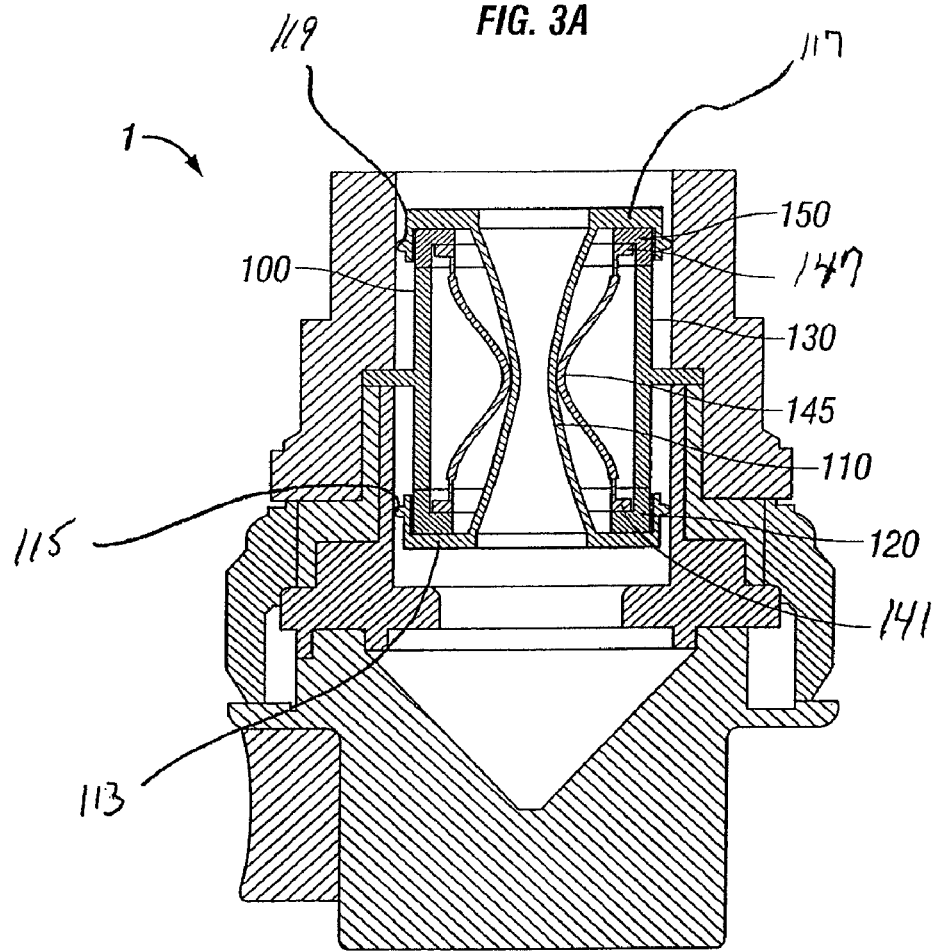
FIG. 3B is a cross-sectional view of the dual seal system illustrating the winepress seal assembly in the first condition.

When initially assembled, winepress assembly 100 may be configured to assume a normal configuration as depicted in FIGS. 3A and 3B. Elastomeric seal 110 is designed to have a relaxed length such that collars 113, 117 press end caps 120, 150 into engagement with the liner 130. In this initial configuration, the spokes 145 are biased to the inclined arrangement shown and the elastomeric seal assumes its most narrow throat diameter. Spokes 145 remain linear or straight, pivoting only at the hinges on each end.

Figure 4A:
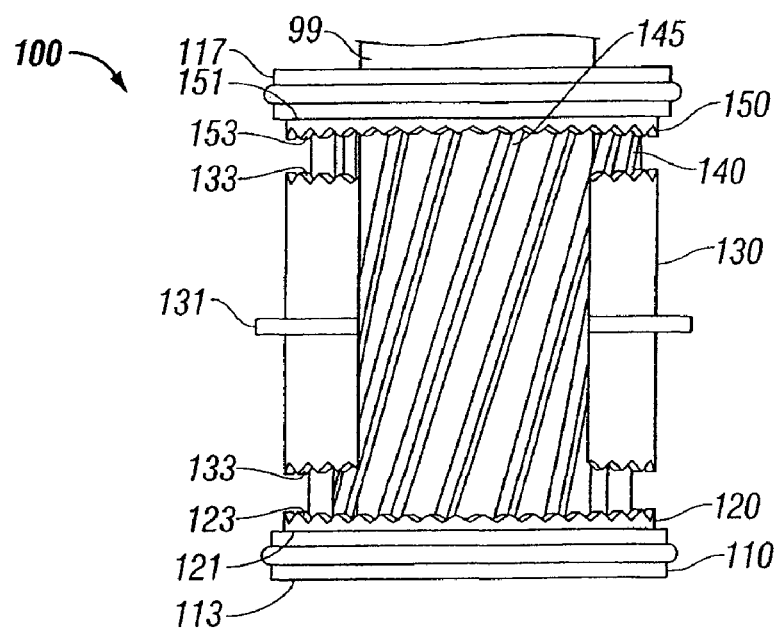
FIG. 4A is a view similar to FIG. 3A illustrating the winepress seal assembly in a second expanded condition to accommodate an instrument.
Figure 4B:
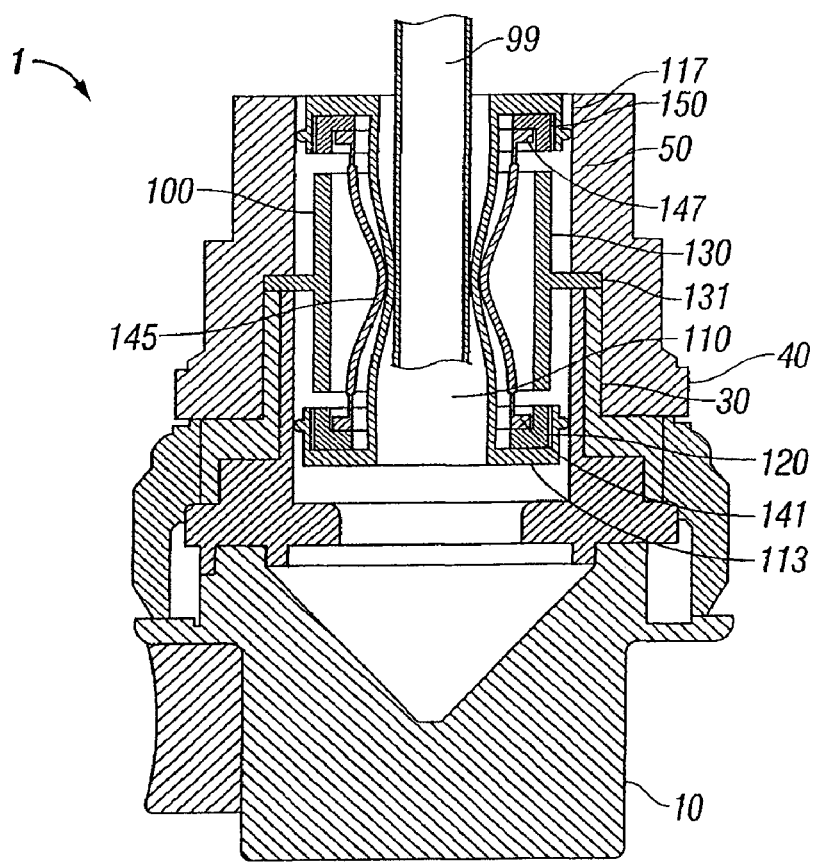
FIG. 4B a view similar to FIG. 3B illustrating the winepress seal assembly in the second condition.

Upon insertion of an elongated object, certain components of winepress seal assembly 100 may be caused to move relative to one another to accommodate the object. In operation, an elongated object such as instrument 99 depicted in FIGS. 4A and 4B, is inserted from the proximal end to engage the minimum diameter section of the throat 111 of elastomeric seal 110. The engagement of teeth 153 on upper end cap 150 with the notches 133 on the stationary liner 130 initially prevents any rotational movement of the end cap 150 and the trailing hub 147. Upon further passage of the instrument 99, the throat 111 widens to accept the instrument 99 with the elastomeric seal 110 pushing radially outwardly against spokes 145. This in turn causes the leading hub 141 to simultaneously translate distally to cause distal displacement of the end cap 120 until a gap is formed between the teeth 123 on the lower end of the end cap 120 and the notches 133 on the distal end of the liner 130. Thus, the leading hub 141 (and lower cap 120) is free to rotate thereby enabling the spokes 145 to move toward a generally linear arrangement to increase the effective internal diameter of the spokes 145. The elastomeric seal 110 no longer constrained by the locked spokes 145 is free to be stretched radially outwardly to stretch the throat 111. It is noted that during insertion of the instrument 99, the teeth 153 of the upper end cap 150 may remain engaged with the notches 133 of the liner 130 due to the distal force placed on the elongated seal 110, and the resulting distal force placed on the upper end cap 150. When the throat 111 has opened sufficiently to accommodate the instrument 99, the natural tendency of the elastomeric seal or seal 110 to return to its initial minimum throat configuration provides the radial pressure required to maintain a seal about the instrument 99. Furthermore, the spokes 145 (again shown in combination in FIG. 4B) may push radially inwardly on the outer surface of the throat 111 of the elongated seal 110 from several directions simultaneously such that the instrument 99 is biased into a general alignment with the central longitudinal axis "k". During manipulation of instrument 99, the elastomeric seal 110, spoke tube 140 and end caps 120, 150 may all translate proximally together with the instrument 99 until a gap is formed on both the proximal and distal sides of stationary liner 130 as seen in FIGS. 4A and 4B. This open throat configuration supports a limited amount of longitudinal translation in either direction until one of the end caps 120, 150 engages the liner 130.

When instrument 99 is withdrawn, the process works in reverse. The withdrawal of the instrument 99 causes the elongated seal 110 to move in a proximal direct due to engagement with the throat 111 of the elongated seal 110. This withdrawal closes the gap between the liner 130 and the lower end cap 120 with the teeth 123,133 of the respective components interlocking. The gap between upper end cap 150 and the liner 130 may be increased. Once the instrument moves past the minimum throat diameter region and disengages from the elastomeric seal 110, the resiliency of the components will cause the trailing hub 147 to rotate under the biasing influence of elastomeric seal 110 and translate distally until winepress 100 returns to the initial minimum throat diameter configuration of FIG. 3A. As the spoke tube 140 transitions from the configuration of FIG. 4A to 3A, the spoke centers will again congregate about the central longitudinal axis "k" pushing inwardly on the minimum diameter region of the elastomeric seal 110. The length of elastomeric seal is again reduced to the relaxed length driving the movement of the other components to make the transition.

In order for the spoke centers to congregate upon the relative translation and rotation of the trailing and leading hubs 141, 147 as described above, the hinges 143 will need to support a complex multi-dimensional pivot of the spokes 145 at each end. A ball-in-socket joint could support this motion allowing a spoke to lean radially inwardly as it also leans longitudinally toward the hub. Because a ball-in-socket joint can be costly to manufacture and maintain due to its complexity, alternatively a living hinge may be used. Generally, a living hinge is a thin and flexible region of the material of a part connecting two more rigid sections of the part allowing for relative motion of the more rigid sections. Because this type of hinge has no frictionally contacting surfaces, it can be designed to have excellent fatigue resistance when formed from a moldable plastic such as polypropylene. Of course any suitable material may be selected for a particular application.

FIGS. 5A and 5B illustrates a spoke tube 240 providing living hinge joints. The living hinges 243 are simply sections of material having a reduced profile when compared to the body of the spoke 245 which connect the leading and trailing hubs 241, 247. The spokes 245 may lean in any direction with respect to the hubs 241, 247 because the flexibility of the material will allow the hinges 243 to bend in any direction. Also evident in FIGS. 5A and 5B is that leading and trailing hubs may be substantially flat and rectangular when initially molded. The flexibility of the material selected will allow the structure to be rolled into a shape similar to the spoke tube 140 in FIG. 2 and to create the necessary passageway through the hubs. A seam 149 will be created on both the trailing and leading hubs. The seam 149 may be joined by any conventional means including an appropriate adhesive which may also be used to join the hubs 141, 147 to the end caps 120, 150. The adhesive or other means used for attachment of the end caps 120, 150 to the hubs 141, 147 should allow no relative motion between either end cap and its respective hub. Because each end cap will move exactly along with its respective hub when so attached, the end caps 120, 150 can be said to become part of the hubs 141, 147.

One other consideration in forming the winepress 100 is the mechanism by which winepress 100 is biased to the normal initial minimum throat diameter. As discussed above, the elastomeric seal 110 is preferably designed with a relaxed length adapted to perform this function. However, other methods may be possible. For example, the spokes 145 may be initially molded obliquely with respect to the hubs 141, 147 such that their natural bias is to the leaned position depicted in FIG. 4A where the spokes 145 have an angle with respect to the central longitudinal axis which is greater than the angle of the spokes depicted in FIG. 3A.

It may be advantageous to incorporate into the winepress assembly 100 a bladed spoke tube 340 having bladed spokes 345 like the one shown in FIGS. 6A and 6B. The bladed spoke 345 is flattened in one direction and remains wide in an orthogonal direction giving each spoke 345 two parallel flat faces 349. The wide direction allows the spoke 345 to maintain some rigidity and resist bending. If the spokes 345 are oriented appropriately, the flattened direction will allow for a closer spacing of the spokes 345 and therefore a greater total number of spokes to be attached to the hubs 341, 347. One characteristic of the spoke tube 140 which limits the number of spokes 145 that may be attached is the minimum throat diameter configuration the spoke tube 140 assumes for the reception of small diameter instruments. To achieve this configuration, the spokes 145 will be in oblique relation to a great extent. Not only will the spoke centers congregate radially toward the central longitudinal axis as discussed above, each spoke center will become crowded by the centers of the neighboring spokes 145 as can be seen in FIG. 3A. For a given minimum throat diameter to be achieved, the abutment of the spoke centers with the neighboring spoke centers limits the number of spokes 145 which may be used. If spokes 145 are too thick and inadequately spaced, the spoke centers will abut one another before both end caps 120, 150 encounters the liner 130 and a sufficiently narrow throat diameter can be achieved. It can be seen then how a bladed spoke 345 can provide a reduced thickness in the proper direction to allow more spokes 345 to be stacked without overcrowding. If oriented and spaced appropriately, the flat faces 349 of the bladed spokes 345 will abut one another when the spoke tube is configured to receive small diameter instruments. This arrangement will allow for a greater number of spokes 345 to be incorporated without requiring the spokes 345 to be too thin to maintain the necessary rigidity. A greater number of spokes 345 may be desirable to create a greater closing force about an instrument or to provide a greater radial support to an instrument.

Finally, the elastomeric seal 110 may be omitted from the winepress assembly 100 creating a centering device that does not sealingly engage an instrument. Without the elastomeric seal 110, the minimum throat diameter is defined by the central portions of the spokes 145. The operation of the spokes 145 would not change except that the elongated object would contact the spokes directly at their midpoints.

Although the foregoing disclosure has been described in some detail by way of illustration and example, for purposes of clarity or understanding, it will be obvious that certain changes and modifications may be practiced within the scope of the appended claims.

What is claimed is:
1. A surgical access apparatus, which comprises: a housing; an access member extending from the housing and defining a longitudinal axis, the access member having a longitudinal passageway for passage of an object and defining trailing and leading ends; and an elongated seal mechanism mounted relative to the housing, the elongated seal mechanism including: a trailing hub and a leading hub longitudinally spaced from the trailing hub, the trailing hub and the leading hub adapted for relative rotational movement about the longitudinal axis; a plurality of spokes pivotally connected to the trailing hub and the leading hub, and extending therebetween in a generally linear manner to define a generally straight spoke, the spokes defining a first minimum internal dimension in a first condition thereof in the absence of an object and defining a second minimum internal dimension in a second condition thereof upon insertion of the object and relative rotation of the trailing hub and the leading hub, the second minimum internal dimension being greater than the first minimum internal dimension; and an elongated seal member disposed within the spokes and adapted to establish a sealing relation about the object wherein the elongated seal mechanism includes an outer liner circumferentially disposed about the spokes and fixed from rotational movement relative to the longitudinal axis, the outer liner engageable with one hub of the trailing and leading hubs during insertion and withdrawal of the object to prevent rotational movement of the one hub whereby the other hub is free to rotate to permit transitioning of the spokes between the first and second condition thereof.

2. The surgical access apparatus according to claim 1 wherein at least two of the spokes are generally obliquely arranged at a first angle relative to the longitudinal axis when in the first condition thereof and are adapted to be generally arranged at a second angle relative to the longitudinal axis when in the second condition thereof, the second angle being less than the first angle.

3. The surgical access apparatus according to claim 2 wherein the trailing hub and the leading hub are adapted for relative longitudinal movement when transitioning of the spokes between the first and second conditions.

4. The surgical access apparatus according to claim 3 wherein the spokes are normally biased toward the first condition thereof.

5. The surgical access apparatus according to claim 4 wherein the seal member is arranged to normally bias the spokes toward the first condition thereof.

6. The surgical access apparatus according to claim 5 wherein the seal member includes trailing and leading collars, the trailing and leading collars adapted to engage the trailing and leading hubs, respectively, to normally bias the trailing and leading hubs in a longitudinal direction toward each other corresponding to the first condition of the spokes.

7. The surgical access apparatus according to claim 1, wherein the outer liner is dimensioned to be engaged by the trailing hub during insertion of the object and cooperates to fix the trailing hub from rotation whereby the leading hub rotates and longitudinally moves relative to the trailing hub to permit the spokes to assume the second condition.

8. The surgical access apparatus according to claim 7 wherein the outer liner is dimensioned to be engaged by the leading hub during withdrawal of the object and cooperates to fix the leading hub from rotation whereby the trailing hub rotates and longitudinally moves relative to the leading hub to facilitate withdrawal of the object.

9. The surgical access apparatus according to claim 8 wherein the outer liner is dimensioned to engage and fix each of the trailing and leading hubs from rotational movement when in the first condition thereof.

10. The surgical access apparatus according to claim 9 wherein the leading hub is adapted to longitudinally move in a leading direction during insertion of the object to disengage the outer liner to thereby rotate relative to the trailing hub and permit the spokes to transition from the first condition to the second condition.

11. The surgical access apparatus according to claim 10 wherein the trailing hub is adapted to longitudinally move in a trailing direction during withdrawal of the object to disengage the outer liner to thereby rotate relative to the leading hub and facilitate removal of the object.

12. The surgical access apparatus according to claim 1 wherein each of the spokes are connected to the leading and trailing hubs by a living hinge.

13. The surgical access apparatus according to claim 1 wherein the spokes are adapted to normally bias the object in general alignment with the longitudinal axis.

* * * * *